United States Patent [19]

Yunoki

[11] Patent Number: 4,670,138

[45] Date of Patent: Jun. 2, 1987

[54] APPARATUS FOR CONTROLLING AN INFINITESIMAL FLOW RATE OF FLUID

[75] Inventor: Toru Yunoki, Chigasaki, Japan

[73] Assignee: Ulvac Service Corporation, Chigasaki, Japan

[21] Appl. No.: 694,065

[22] Filed: Jan. 23, 1985

[30] Foreign Application Priority Data

Jan. 25, 1984 [JP] Japan .................................. 59-10311

[51] Int. Cl.⁴ .............................................. B01D 21/30
[52] U.S. Cl. .................................. 210/141; 210/198.2
[58] Field of Search ................... 210/87, 101, 134, 97, 210/198.2, 104; 137/557, 558; 55/67, 133, 197, 484

[56] References Cited

U.S. PATENT DOCUMENTS

| 3,121,681 | 2/1964 | Baxter | 210/104 |
| 3,491,512 | 1/1970 | Timmins et al. | 55/67 |
| 4,083,661 | 4/1978 | McPherson et al. | 210/104 |
| 4,226,714 | 10/1980 | Furness et al. | 210/104 |
| 4,422,942 | 12/1983 | Allington | 210/101 |
| 4,448,692 | 5/1984 | Nakamoto et al. | 210/101 |

Primary Examiner—Andrew H. Metz
Assistant Examiner—Sharon T. Cohen
Attorney, Agent, or Firm—Larson and Taylor

[57] ABSTRACT

Apparatus for controlling an infinitesimal flow rate of fluid comprises at least one filter means (3, 3A, 3B, 3C, 3D, . . . ) provided in a fluid passage and capable of setting to a predetermined filtration amount, thereby regulating the flow rate of the fluid by controlling fluid supply to said filter means. The present apparatus may be used in a vacuum processing system.

13 Claims, 5 Drawing Figures

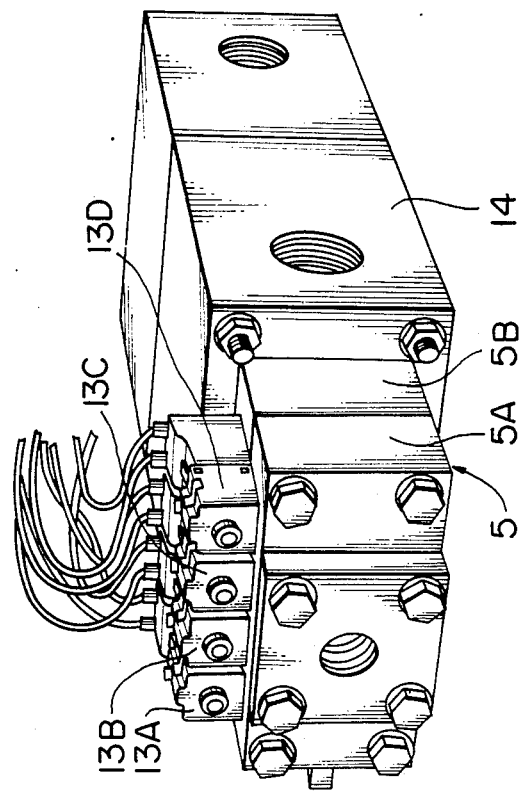

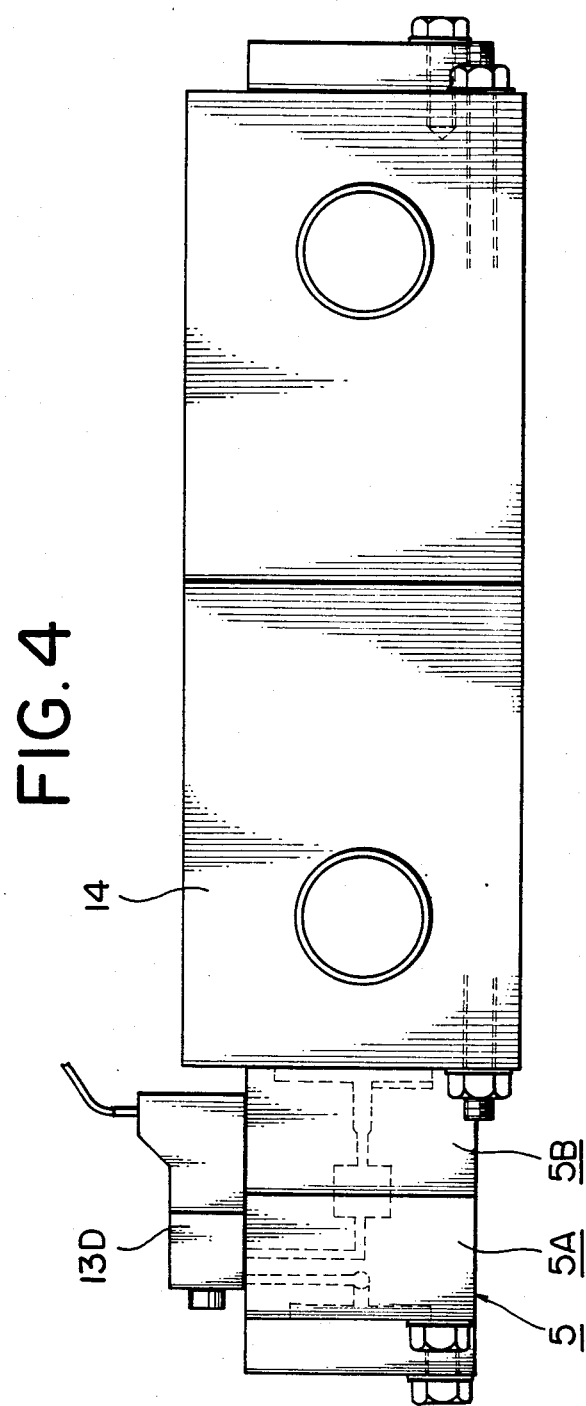

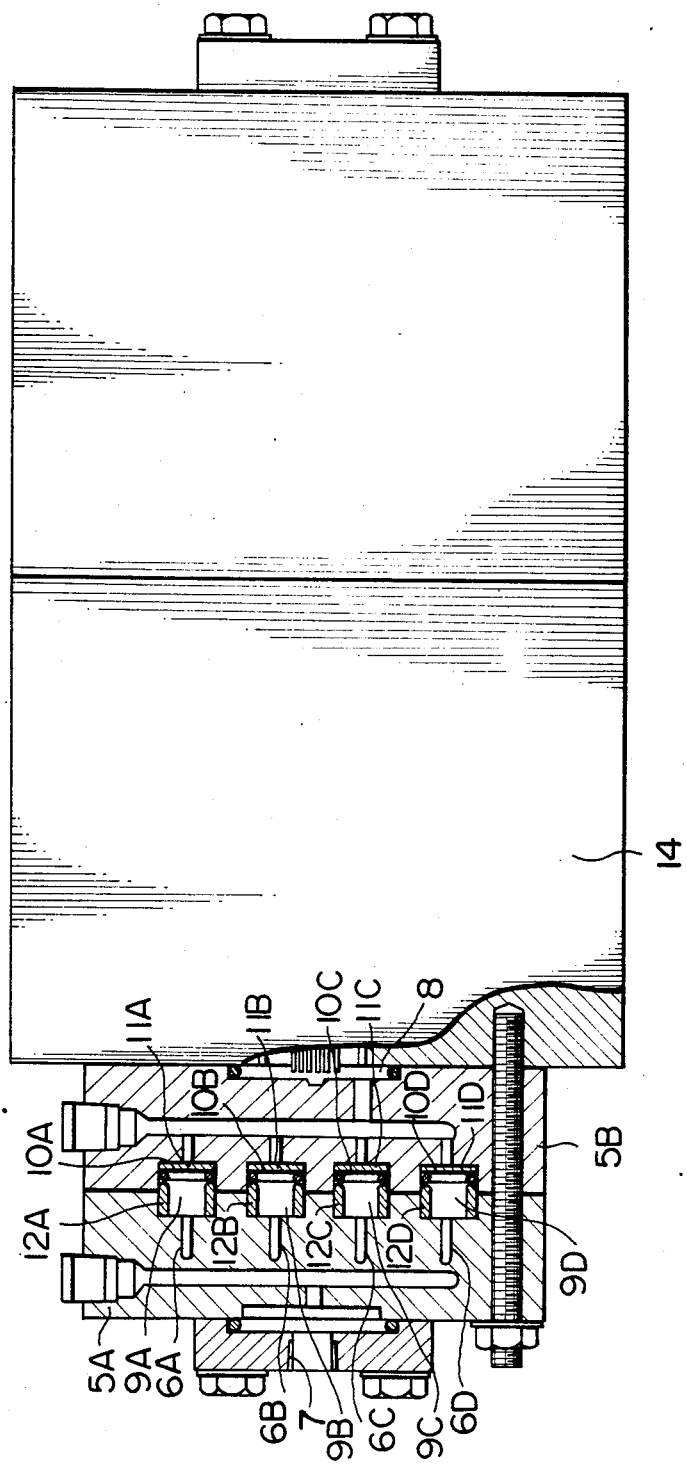

APPARATUS FOR CONTROLLING AN INFINITESIMAL FLOW RATE OF FLUID

DESCRIPTION

The present invention relates to an apparatus for controlling an infinitesimal flow rate of fluid (e.g., gas), which may be used in control of a reaction gas flow rate for CVD (chemical vapour deposition), control of a predetermined leakage in a performance test of a vaccum pump, or control of a flow rate in a gas chromatography.

As known, it is generally difficult to control an infinitesimal flow rate of fluid such as gas by using manually operated valves. Therefore, such flow rate control of very small flow was heretofore performed by means of an automatic regulation with automatic control valves. However, such automatic control valves for an infinitesimal flow rate control are expensive and bulky, and thus the regulator apparatus itself leads to large size and expensive cost.

It is, therefore, an object of the present invention to provide an apparatus for controlling an infinitesimal flow rate of fluid which is simple and inexpensive by using a filter capable of setting filtration amount (i.e. permeation amount) instead of the automatic regulating valve heretofore used.

Another object of the invention is to provide an apparatus for controlling an infinitesimal flow rate of fluid using a filter assembly having variable filtration amount which may be controlled in response to a predetermined programme.

A further object of the invention is to provide an apparatus for controlling an infinitesimal flow rate of fluid using a filter assembly which comprises a plurality of parallel connected filters, each filter having different filtration amount one another.

Still another object of the invention is to provide an apparatus for controlling an infinitesimal flow rate of fluid which is to be used in a vacuum processing system.

SUMMARY OF THE INVENTION

According to the present invention there is provided an apparatus for controlling an infinitesimal flow rate of fluid comprising filter means provided in a fluid passage and capable of setting to a predetermined filtration amount and means for controlling fluid supply to said filter means, thereby regulating the infinitesimal flow rate of fluid.

In a preferred embodiment, said filter means comprises at least one filter provided in the fluid passage, and said fluid supply control means includes valve means which is arranged to regulate the pressure of fluid to be supplied to each filter.

In another embodiment, said filter means comprises a plurality of filters which are disposed in paralled with the fluid passage to form parallel branch passages and respectively have different filtration amounts. The branch passages of the filters can be opened and closed by means of solenoid valves which are respectively provided at the inlet sides of the respective filters.

It is preferred that the filter means and the solenoid valves may be constructed as a single unit.

BRIEF DESCRIPTION OF THE DRAWINGS

The above and other objects, features, and advantages of the present invention will become apparent upon consideration of the following detailed description of one specific embodiment thereof, especially when taken in conjunction with the accompanying drawings.

FIG. 3 is a perspective view showing an application of the apparatus illustrated in FIG. 2 combined to a high purity solution producing device;

FIG. 4 is a front view of the arrangement of FIG. 3;

FIG. 5 is a sectional plan view of the arrangement illustrated in FIG. 3.

DETAILED DESCRIPTION

Figure 1:
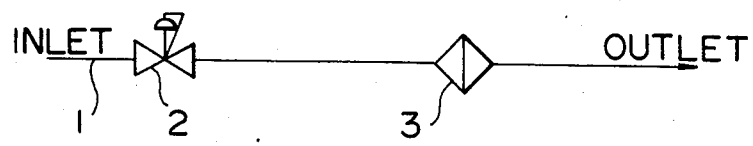
FIG. 1 is a shematic diagram showing a flow rate controlling apparatus in accordance with one embodiment of the present invention.

Reference is now made to FIG. 1 of the drawings wherein an embodiment of the present invention is shown. Reference numeral 1 designates a gas flow passage, 2 a pressure reducing valve, and 3 a filter. The pressure of the inflowed gas is regulated by the valve 2, thereby varying the flow rate to an outlet through the filter 3. The filter 3 is constructed to flow the fluid at a predetermined flow rate within the pressure range readily regulated by the valve 2. In other words, the used filter 3 has preferably a certain degree of resistance to the filtration of gas, and the diameter and area of the filtration hole in the filter 3 can be selected according to the flow rate of the gas. Preferably, the hole diameter of the applied filter may be 0.05 to 0.5 microns, and the flow rate range may be set to 0 to 1 liter/min.

For example, the relationship between the gas pressure and the filtration amount when a filter having 0.1 micron in diameter is used is shown in Table 1, and the relationship between the area of the filter and the filtration amount (having a pressure of 0.1 kg/cm$^2$) is shown in Table 2.

TABLE 1

| Pressure (kg/cm$^2$) | 0.014 | 0.035 | 0.048 | 0.062 |
|---|---|---|---|---|
| Filtration amount (ml/cm$^2$-min.) | 9 | 24 | 31 | 43 |

TABLE 2

| Area (cm$^2$) | 0.16 | 0.38 | 0.69 | 0.89 |
|---|---|---|---|---|
| Filtration amount (ml/min.) | 12 | 23.5 | 47 | 60 |

As apparent from the above Tables 1 and 2, the pressure and the filtration amount (per units area) as well as the area and the filtration amount are respectively substantially proportional in variation.

Figure 2:
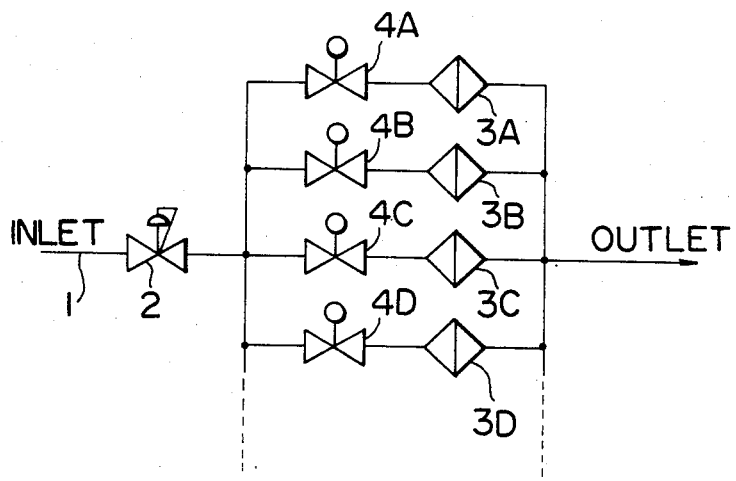
FIG. 2 is a shematic diagram showing another embodiment of the present invention.

Referring to FIG. 2, there is shown another embodiment of the present invention. In this embodiment, a number of filters 3A, 3B, 3C, 3D, . . . are disposed in parallel, and solenoid valves 4A, 4B, 4C, 4D, . . . are respectively provided at the inlet sides of the respective filters 3A, 3B, 3C, 3D, . . . . The filters respectively have different filtration amounts (permeable amounts). For example, the first filter 3A is 1, the second filter 3B is ½, the third filter 3C is ¼, and the fourth filter 3D is ⅛ at the ratio. Such a ratio can be arbitrarily provided by altering the area or the diameter of pores of the filter or superposing the filters. Any flow rate may be adjusted by operating the solenoid valves 4A, 4B, 4C, 4D, . . . inserted before the filters by controllers (not shown), thereby performing an automatic control. Further, the pressure reducing valve 2 serves to maintain the pressure constant in this case. In other words, when all the valves 4A to 4D are opened, the maximum flow rate can be obtained, while when all the valves 4A to 4D are closed, the flow rate becomes zero. Therefore, the flow rate can be determined from zero to the maximum flow rate in combination of the opened solenoid valves. The resolution depends upon the number of the filters used. For example, when four filters are used, 16 stages of controls can be performed. In other words, when the opened valve is "1" and the closed valve is "0", it can be represented as the binary number from 0 to 15. Further, the opening or closing of the valves 4A to 4D can be controlled directly by a digital signal. A number of filters having equal filtration amount may be used as required, similar operation can be performed by varying the number of the filters in the branch passages.

Referring to FIGS. 3 to 5, there is shown the structure of the apparatus of FIG. 2 which is used to a high purity solution producing device. Infinitesimal flow rate control apparatus according to the present invention is designated by reference 5, and comprises two manifold members 5A and 5B which are fixed to each other by means of fastening bolts. As will be seen in FIG. 5, four parallel fluid branch passages 6A, 6B, 6C, 6D are provided between an inlet 7 and an outlet 8 for fluid in the manifold members 5A and 5B. Each branch passage (6A-6D) is provided with a filter chamber (9A-9D) into which a filter (10A-10D) is inserted. That is, the filters 10A-10D are tightly supported against porous plates 11A-11D by sleeves 12A-12D, respectively. The filters 10A-10D in the respective filter chambers 9A-9D are respectively formed by filter elements having different filtration amounts. Each of the branch passages is connected at the inlet sides of the filter chambers to the corresponding one of electromagnetic valves 13A, 13B, 13C and 13D which are mounted on the manifold member 5A. The unit thus assembled is mounted on the body 14 of a high purity solution producing device.

According to the present invention as described above, the infinitesimal flow rate of the fluid can be controlled without using a conventional expensive automatic regulating valve, and the flow rate can be regulated in a wide range by suitably selecting the filters, and when a computer is further employed, the flow rate can be directly controlled.

While the present invention has been described in detail with respect to a certain now preferred embodiment of the invention, it will be understood by those skilled in the art that various changes and modifications may be made without departing from the spirit and scope of the invention, and it is intended, therefore, to cover all such changes and modification in the appended claims.

What is claimed is:

1. An apparatus for controlling an infinitesimal flow rate of gas between an inlet and an outlet so as to regulate the infinitesimal flow rate at the outlet, said apparatus comprising a filter means, said means comprising a plurality of filters which are respectively connected in a like plurality of parallel branch passages for the gas located between said inlet and said outlet each providing an amount of filtration for controlling the rate of gas flow between the inlet and the outlet, and a control means for controlling opening and closing of said branch passages to vary the numbers of plurality of filters connected between said inlet and outlet and to thereby regulate the infinitesimal flow rate of gas out of said filter means and thus regulate the infinitesimal flow rate at said outlet.

2. An apparatus as in claim 1 in which said parallel branch passages respectively provide different amounts of filtration.

3. An apparatus as in claim 2 in which control means includes a plurality of solenoid valves for selectively controlling the opening or closing of the filter branch passages.

4. An apparatus as in claim 2 in which at least two of said plurality of solenoid valves are simultaneously operated to open or filter branch passages associated therewith.

5. An apparatus as in claim 4 in which the operation of each of the solenoid valves is controlled by a programmable control system.

6. An apparatus as in claim 2 in which the amount of filtration provided by the filter disposed in each branch passage is determined by the area of the filter.

7. An apparatus as in claim 2 in which the amount of filtration provided by the filter disposed in each branch passage is determined by the diameter of the pores of the filter.

8. An apparatus as in claim 2 in which the amount of filtration provided by the filter disposed in each branch passage is determined by the area of the filter and the diameter of pores of the filter.

9. An apparatus as in claim 2 in which the filter in each branch passage includes at least one filter element, each said filter element providing the same amount of filtration, and the amount of filtration provided by the filter in each branch passage is set by varying the number of the filter elements used.

10. An apparatus for controlling an infinitesimal flow rate of gas between an inlet and an outlet so as to regulate the infinitesimal flow rate at the outlet, said apparatus comprising a filter means, which is disposed in a passage for the gas between the inlet and the outlet and which provides an amount of filtration dependent upon the pressure of the gas, for controlling the rate of gas flow between the inlet and the outlet, and a control means for controlling the pressure of the gas supplied to said filter means to control the amount of filtration provided by the filter means to thereby regulate the infinitesimal flow rate of gas out of said filter means and thus regulate the infinitesimal flow rate at said outlet.

11. An apparatus as in claim 10 in which said control means includes a pressure reducing valve which is disposed in an inlet passage for the gas.

12. An apparatus as in claim 11 in which the pressure of the fluid which is fed to the filter means is maintained constant by the pressure reducing valve.

13. An apparatus as in claim 10 in which the gas whose flow rate is to be controlled is a reaction gas for a chemical vapor deposition system.

* * * * *